(12) United States Patent
Lundbäck

(10) Patent No.: US 8,560,057 B2
(45) Date of Patent: *Oct. 15, 2013

(54) STATE MACHINE INTERFACE SYSTEM

(75) Inventor: Stig Lundbäck, Vaxholm (SE)

(73) Assignee: Gripping Heart AB, Stockholm (SE)

( * ) Notice: Subject to any disclaimer, the term of this patent is extended or adjusted under 35 U.S.C. 154(b) by 975 days.

This patent is subject to a terminal disclaimer.

(21) Appl. No.: 12/303,154

(22) PCT Filed: May 28, 2007

(86) PCT No.: PCT/SE2007/050366
§ 371 (c)(1),
(2), (4) Date: Jun. 12, 2009

(87) PCT Pub. No.: WO2007/142594
PCT Pub. Date: Dec. 13, 2007

(65) Prior Publication Data
US 2010/0030094 A1    Feb. 4, 2010

(30) Foreign Application Priority Data
Jun. 2, 2006   (SE) .................................... 0601243

(51) Int. Cl.
*A61B 5/044* (2006.01)
(52) U.S. Cl.
USPC ............................ 600/513; 600/508; 600/523
(58) Field of Classification Search
USPC ........................................................ 600/508
See application file for complete search history.

(56) References Cited

U.S. PATENT DOCUMENTS

| | | | |
|---|---|---|---|
| 5,151,856 A | 9/1992 | Halmann et al. | |
| 5,431,691 A | 7/1995 | Snell et al. | |
| 5,947,899 A | 9/1999 | Winslow et al. | |
| 5,974,341 A | 10/1999 | Er et al. | |
| 6,052,618 A * | 4/2000 | Dahlke et al. | 600/523 |
| 6,485,431 B1 * | 11/2002 | Campbell | 600/526 |
| 6,743,172 B1 * | 6/2004 | Blike | 600/300 |
| 6,754,580 B1 | 6/2004 | Ask et al. | |

(Continued)

FOREIGN PATENT DOCUMENTS

| | | |
|---|---|---|
| JP | 2003199715 A | 7/2003 |
| JP | 2003533309 A | 11/2003 |

(Continued)

OTHER PUBLICATIONS

International Search Report dated Jun. 29, 2007, from corresponding PCT application.

(Continued)

*Primary Examiner* — Kennedy Schaetzle
(74) *Attorney, Agent, or Firm* — Young & Thompson

(57) ABSTRACT

State machine interface system, heart state machine analyzer and/or stimulator, comprising state machine algorithms and a graphical user interface, adapted to receive signals from a sensor device that are related to physiological activities of the heart and/or the circulatory system of a living being and the state machine algorithms determine states of heart cycles based upon the signals. The determined heart cycle states are graphically presented at the graphical user interface such that the temporal relation between the different states are illustrated. The graphical user interface may be circular diagrams or bar graphs including parts representing the temporal relation between the different states.

15 Claims, 8 Drawing Sheets

1  Prog/Reg Atrial Contribution
2  Volume to Tension, M/TRI closing
3  Prog/Reg Outlet
4  Tension to Volume
5  Prog/Reg Rapid AV-Filling
6  Slow AV-Filling

LEFT VENTRICLE
RIGHT VENTRICLE

(56) References Cited

U.S. PATENT DOCUMENTS

| | | | |
|---|---|---|---|
| 6,772,004 B2 * | 8/2004 | Rudy | 600/509 |
| 6,778,852 B2 * | 8/2004 | Galen et al. | 600/523 |
| 7,054,679 B2 * | 5/2006 | Hirsh | 600/523 |
| 7,113,450 B2 * | 9/2006 | Plancon et al. | 368/10 |
| 7,225,011 B2 | 5/2007 | Mielekamp | |
| 7,310,551 B1 * | 12/2007 | Koh et al. | 600/523 |
| 2003/0166991 A1 | 9/2003 | Landback et al. | |
| 2005/0202384 A1 | 9/2005 | DiCuccio et al. | |
| 2005/0277813 A1 | 12/2005 | Katz et al. | |
| 2008/0154142 A1 * | 6/2008 | Lundback | 600/508 |

FOREIGN PATENT DOCUMENTS

| | | |
|---|---|---|
| JP | 2004202250 A | 7/2004 |
| JP | 2004519306 A | 7/2004 |
| WO | 01/88642 | 11/2001 |
| WO | 0188642 A1 | 11/2001 |
| WO | 02/32035 | 4/2002 |

OTHER PUBLICATIONS

Japanese Office Action dated Jun. 19, 2012, from corresponding JP application.

* cited by examiner

STATE MACHINE INTERFACE SYSTEM

FIELD OF THE INVENTION

The present invention is based upon the insight that the heart appears in its pumping function more like a piston pump or a pressure and suction pump and even more precise as a cluster state machine of finite muscle cell state machines and DeltaV-pump machines forming the DeltaV heart pump with abilities to be controlled by inflow. Knowing the true pumping and regulating functions of a normal functioning heart over the whole register of pressure, flow in and out-through the heart at varying frequencies and inotropic conditions, it will be possible to generate functional state diagrams to detect disturbances, good, normal and bad performances of the pumping and regulating functions of the heart. Optionally this may be done down to the micro level of a muscle cell state machines and as a pump in a closed circulatory system. PCT/SE2006/000114 (international filing date 25 Jan. 2006), assigned to the applicant of the present application, relates to a heart cluster state machine applicable to simulate the pumping and regulating functions of the heart and the circulatory system.

The state machine interface system, according to the present invention, is applicable in relation with a large number of various medical investigating methods and devices.

BACKGROUND OF THE INVENTION

It is asserted in the theses Lundbäck S., "Cardiac Pumping and Function of the Ventricular Septum", Stockholm, 1986, that the pumping and regulation of the human heart take place in a manner which is at variance with the prevalent view.

According to the cited publication, the healthy heart performs its pumping action without substantially changing its outer shape and volume.

As a result of the theory presented in the above-mentioned publication regarding the heart's pumping and regulating function a new class of pumps has emerged, a so called dynamic displacement pump or delta ($\Delta$) volume pump (abbreviated as $\Delta$V-pump). The principles of a $\Delta$V-pump will now be described with references to FIGS. 1a and 1b. The pump comprises an upper cylinder 2 with diameter d1 and a lower cylinder 4 with diameter d2, where d2>d1. These two cylinders are connected to each other via a third cylinder 6 that is freely movably arranged between the upper and lower cylinders. The movable cylinder 6 is provided with a valve 8 at its lowest part that corresponds e.g. to the mitralis valve in the heart. The volume above this valve is defined as the atrial volume (Va) and the volume below the valve is defined as the ventricular volume (Vv). The lower cylinder is provided with an outflow valve 10 at its lowest part that corresponds e.g. to the aortic valve in the heart. As can be seen from FIG. 1b is a ring-shaped cylindrical volume gradually obtained between the movable cylinder and the inner wall of the lower cylinder when the movable cylinder is moved down, $\Delta$V in the figure. This results in that the volume Va+Vv decreases with the volume $\Delta$V when the movable cylinder moves between its upper position and its lower position.

A source of energy (not shown in the figures) is adapted to move the movable cylinder from its upper position to its lower position, which defines the length L of a stroke for the pump. When the movable cylinder moves down to its lowest position the outflow valve is forced to open and a part of volume Vv is expelled. The movable cylinder is then released from the source of energy and can return to its upper position if there is an inflow to the pump. If Av and Aa designates the cross-sectional areas of the upper and lower cylinder, respectively, $\Delta$V equals L(Av−Aa).

WO-01/88642 relates to a computer based system adapted to create a representation of the pumping action of a heart by using a mathematical model of the functions of the heart based upon the above-described principles of the $\Delta$V-pump in order to make it possible to enhance the methods of analyses, diagnosis and therapy of the heart. The heart is modelled by a computer-based representation of one dynamic displacement pump or of two interconnected dynamic displacement pumps, $\Delta$V-pumps.

Many different requirements, boundary conditions, must generally be met when implementing a mathematical model on to a pump, describing its construction, power source, pumping and regulating functions in a circulatory system. There will be even more boundary conditions if the circulatory system comprises two circulatory systems, as is the case with the heart, and pumps, where the flow to and from the two circulatory systems always shall be in balance.

Usually individual's heart and circulatory system are investigated at rest when flow, frequencies and inotropic stimuli are low. Most of all reference values telling if the heart and the circulatory system is in a good or bad position are found and compared during idling pumping motions of the heart. During these circumstances the heart cycle is long and the energy absorbing, and energy to mechanical converting, characteristics of the DeltaV-principles are less pronounced for the pumping, filling and regulating functions of the heart. This may be one of the reasons why the squeezing pumping functions of the heart together with the regulating functions of the "Frank-Starling law" as a lost motion squeezing displacement pump, have been established as a platform for heart and circulatory diagnostics of today.

New investigating methods like MRI (Magnetic Resonance Imaging) and Spin CT (Spinning Computer aided Tomography), and further developments within the ultra sound technique with TVI (Tissue Velocity Imaging) and reflector based velocity imaging (2D strain) with reduced visualization of false movements, have shown that the heart mainly is pumping with back and forth motion of the AV (Atria-Ventricular)-plane. The DeltaV-functions are not yet understood, even though heavy discussions have started to explain what kind of forces there are acting on the ventricular filling. Terms like Diastolic heart failure have become a popular scientific discussion subject. What gives the heart its regulating functions within the new insight of a piston like pumping function has not yet become a discussion subject.

Investigations of the heart with old or new investigating methods bring a lot of information that may be very hard to interpret. Every mechanical subject can be expressed in state diagrams with known interrelations if the mechanics behind these working principles is known. That is not fully known concerning the heart as a mechanical unit. This is especially the case regarding the filling and regulating functions of the heart. The complex architecture of the heart, the rotating and the resilient suspension, especially against the diaphragm and sliding motions towards sternum, external and internal volume changes, especially at the DeltaV areas, together with unknown mechanics of the heart, makes it almost impossible to determine the contributions of different activities within the heart even at very low flow and heart rates. At higher flow and heart rates, all investigating methods, more or less, shows a chaotic output of information. This, together with the general belief that the heart is pumping with squeezing functions, are probably the reasons why the analysis of physiological activities concerning the heart and the circulatory system is a time-consuming and difficult procedure.

Thus, the general object of the present invention is to achieve a tool that may be used to interpret the outputted information in a cost-efficient, fast and reliable way and also make it accessible for analysis and diagnosis.

Specifically, one object of the present invention, knowing the true pumping and regulating functions of the heart, is to describe physiological activities from the heart and/or the circulatory system of an individual organized to generate different states of the heart cycle, wherein said different states are presented graphically by the interface such that the temporal relation between the different states are illustrated as state diagrams of the hearts pumping and regulating functions.

Another object is to generate local and/or global information systems that can support and analyze the states in preferred state diagrams.

Thus, the overall object of the present invention is to achieve a state machine interface system including a graphical user interface that is cost-efficient and accurate in obtaining validated diagnosis, prognosis, medical and surgery treatments (reconstructive heart surgery with artificial and or biological materials) and follow up studies for patients, health-care and training athletes.

SUMMARY OF THE INVENTION

The above objects are achieved by a state machine interface system according to the independent claim, preferred embodiments are set forth in the dependent claims.

The invention is based upon the insight that the heart is pumping as a piston pump or a pressure suction pump, and that the heart in addition acts in a new class of pumps, Dynamic Displacement Pumps (DeltaV-pumps) taking care of the hearts regulating functions and helps to bring the piston back. Actually the heart can be said to work like a cluster state machine of finite muscle cell state machines and DeltaV-pump state machines, creating the DeltaV-heart pump. By using the state machine interface system according to the invention it is possible, with any kind of investigating method, to run an automatic detection of physiological activities from the heart, its surroundings and/or the circulatory system of an individual. The interface system organizes and transforms these activities to generate different states of the heart cycle, wherein the different states graphically are presented by the interface such that the temporal relation between the different states are illustrated as a state diagram of the hearts pumping and regulating functions.

The heart's pumping and regulating functions may automatically on line with a graphic user interface be presented as state diagrams that broadens the diagnostics, clarifies all chaotic motions of the heart especially at high heart rates and flow, and can serve as a final document for the functions of the heart. A complete, or partly complete, state diagram is easily evaluated, manually and/or automatically, by local and or global information systems.

State diagrams that only have time related states can theoretically be found anywhere inside and outside the heart and circulator system.

In this way even simple investigating tools like accelerometers placed outside the body (e.g. pulse and apex cardiogram), blood pressure units etc. can be used to generate state diagrams that will be easy to use, interpret and communicate (telemedicine) with local and/or global information systems.

SHORT DESCRIPTIONS OF THE APPENDED DRAWINGS

The present invention will now be described in detail with references to the appended drawings.

FIGS. 1a and 1b schematically illustrates the principles of a ΔV-pump.

Figure 4:
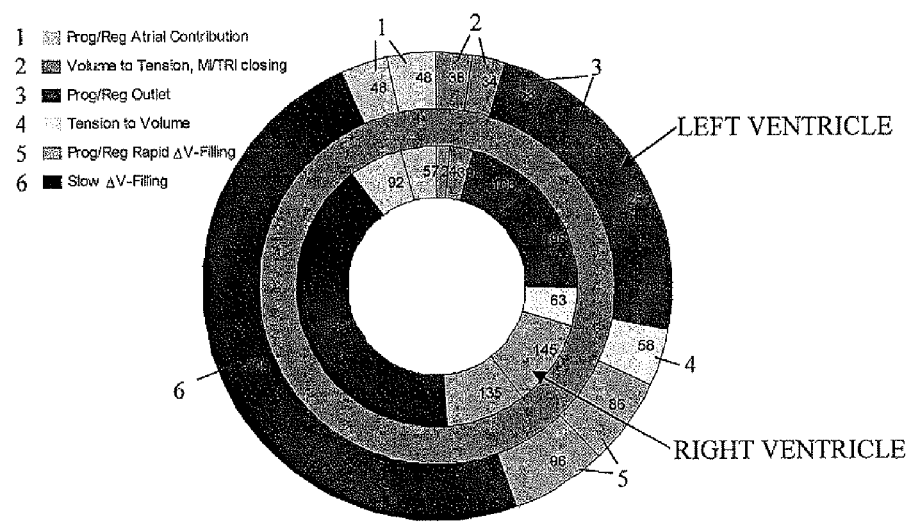

FIG. 4 schematically illustrates the graphical user interface according to a first preferred embodiment of the present invention.

Figure 5:
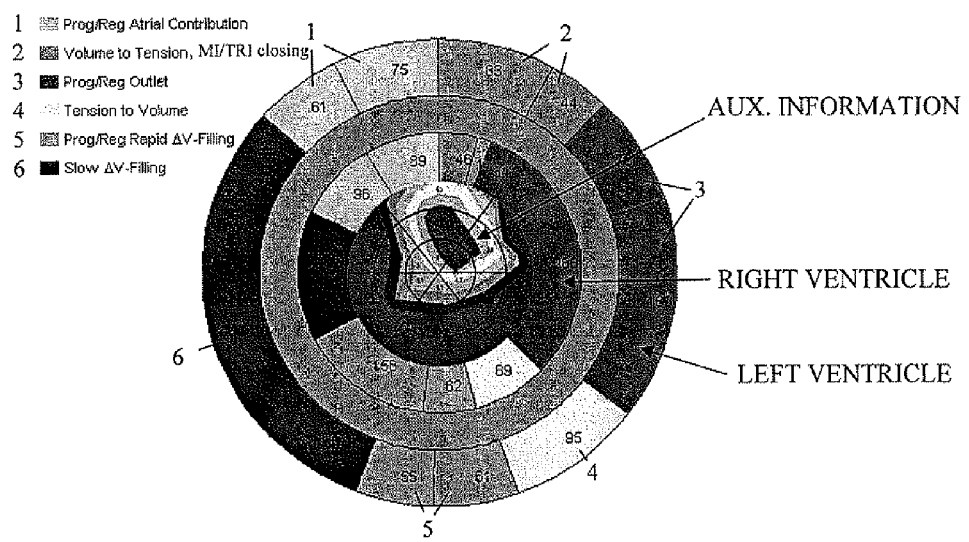

FIG. 5 schematically illustrates the graphical user interface according to a second preferred embodiment of the present invention.

Figure 6:
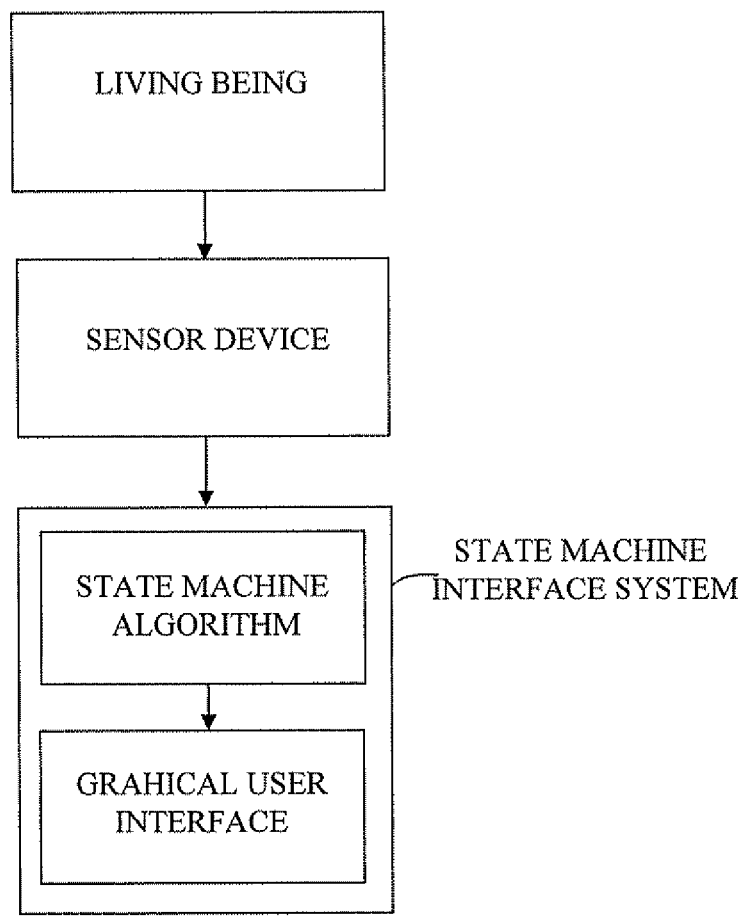

FIG. 6 is a schematic block diagram of the state machine interface system according to the present invention.

Figure 7:
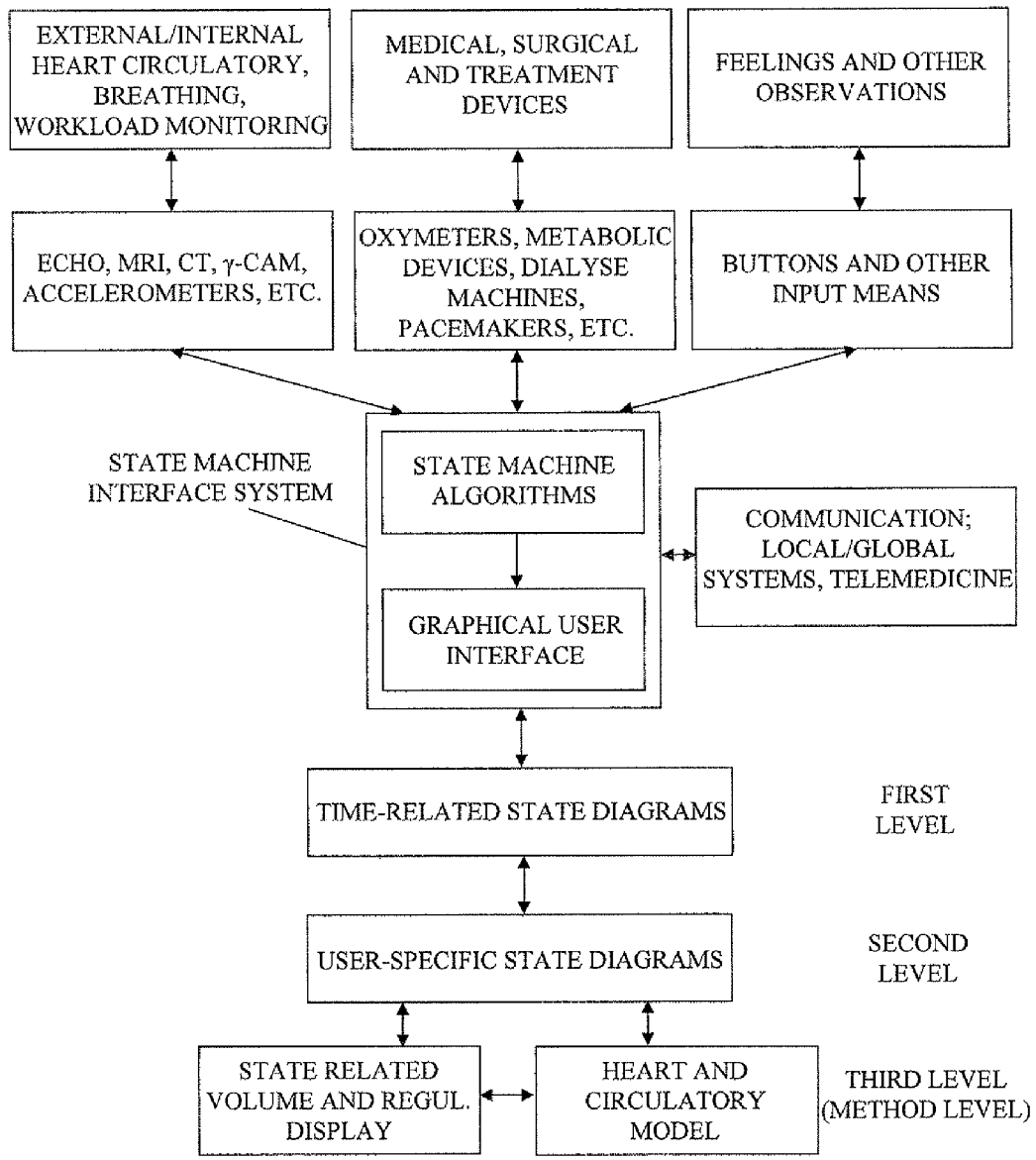

FIG. 7 is a schematic block diagram generally illustrating the functional relationships between the state machine interface system according to the present invention and systems/devices interacting with the interface system.

FIGS. 8A-8D illustrate examples of 3D-representations of a heart, achieved in accordance with the present invention.

Figure 9:
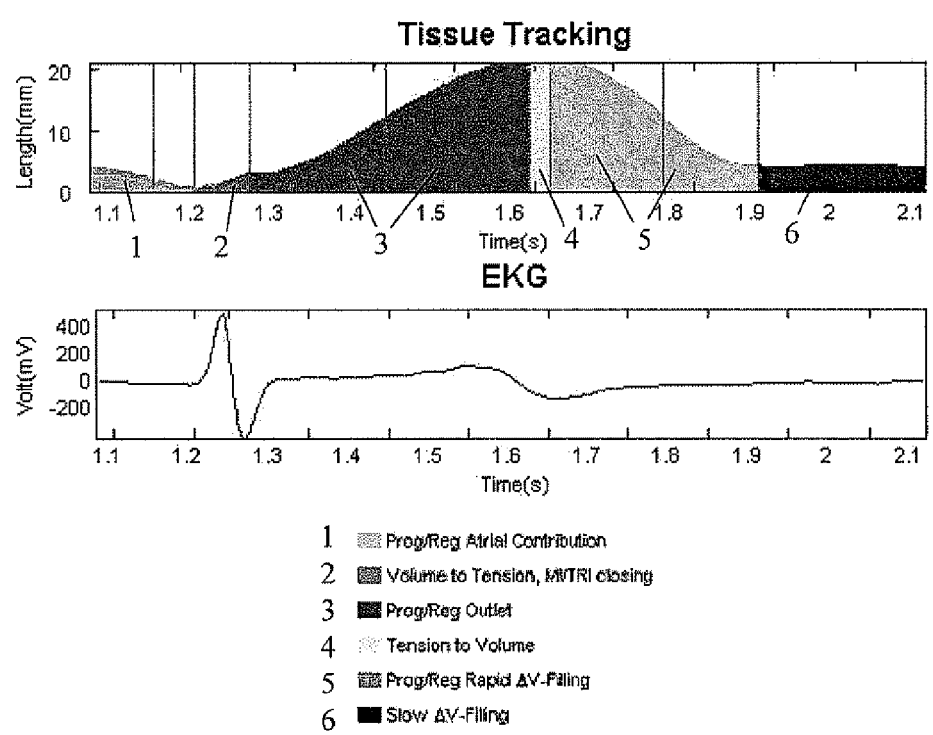

FIG. 9 schematically illustrates the graphical user interface according to a third preferred embodiment of the present invention.

DETAILED DESCRIPTION OF PREFERRED EMBODIMENTS OF THE INVENTION

In order to fully describe all aspects of the present invention it is considered necessary to include, in the following, parts of the detailed description of the above-identified PCT-application (PCT/SE2006/000114).

The key to reproduce the heart and its functions is to define the fundamental boundary conditions that Nature has been able to fulfill, creating the pumping and regulating functions of the heart.

According to the underlying principles behind the present invention this is achieved by transforming the heart in technical terms to a heart cluster state machine running with the dynamic boundary conditions that normally are set by Nature. The heart cluster state machine is a result of fusions of dynamic boundary conditions of finite heart muscle cell state machines to a muscular network, the heart muscle, adapted to the dynamic boundary conditions of a ΔV-pump state machine. The created heart cluster state machine also being referred to as the ΔV-heart pump, will follow the dynamic boundary conditions of said finite heart muscle cell state machine and of said ΔV-pump state machine.

The working condition of the cluster state machine will be equal to the working conditions of the heart inside a body and may be expressed by databases, preferable relational databases, by using generally available computing, imaging, storage, and analysing systems.

As briefly discussed above, instead of pumping with squeezing functions being the traditional pumping movement of the heart, the present invention is based upon the observations that the heart is pumping with back and forth going movements with a piston-like unit, referred to as the Delta (Δ) V-piston or the spherical AV-piston. The area of the piston consists of a more flat area and a curved area. The flat area consists of the ring of annulus fibrosis, the AV-ring, and its four valves which means that it includes the connection areas of aorta and the pulmonary artery T. Pulmonalis.

The curved area being convex in two-dimensional imaging or spherical in three-dimensional imaging consists of the left and right muscles connected to the flat area, the ring of annulus fibrosis.

When the $\Delta V$-piston is drawn towards the apex of the heart and forces the blood contained in the ventricles into the pulmonary and systemic circulation, it will at the same time draw blood into the atria and its auricles as a consequence of the boundary conditions of the $\Delta V$ heart pump. The convex parts, areas, of the $\Delta V$-piston that are in direct contact with the pericardia including the projected areas of Aorta and Pulmonalis that are in direct contact with the surrounding tissues will form the direct $\Delta V$ volumes. The areas of the $\Delta V$-piston that are in indirect contact with the surrounding volumes will form the indirect $\Delta V$-volumes. Such areas are mostly covered by the auricles and to a certain extent T. Pulmonale and Aorta.

During the beginning of ventricular diastole, during the phase when the ventricular muscles start to be relaxed, the $\Delta V$-piston starts to return to its the initial position by filling up the $\Delta V$ volumes it generated during the contraction of the ventricles. That is done under influence of dynamic and static forces of the masses and by stored energy in the heart structures and its surroundings, created by the downward movement of the $\Delta V$-piston during ventricular systole. The pressure gradients over the $\Delta V$ areas generate a hydraulic return of the $\Delta V$-piston, and is referred to as the $\Delta V$-function.

Most of the outer volume changes are the direct and indirect $\Delta V$ volumes in connection to the motion of the $\Delta V$-piston. The abilities (as described in the cited theses) of the heart to change the relative volumetric capacities of the right and left ventricles are mainly done by motions of the common ventricular wall, the ventricular septum. During ventricular diastole the relaxed state of the muscles the ventricular septum can adapt its form and position depending of the pressure gradients between the two ventricles. During ventricular systole the ventricular septum together with the rest of the left ventricular heart muscle assumes an essentially cross circular cross-sectional configuration and takes a distinct position independently of its shape and position during diastole. This is so, because during ventricular systole the pressure in the left ventricle is always higher than the pressure in the right ventricle. If the configuration and position of the ventricular septum during diastole, the relaxed state, are different from the configuration and position during systole, the active state, the ventricular septum, acting like a diaphragm pump, therefore provides an increased stroke volume for one ventricle and a correspondingly reduced stroke volume for the other ventricle. In this way, the ventricular septum accomplishes a double-acting regulation to maintain the balance between the two branches of the circulatory system (the pulmonary circulation and the systemic circulation).

The dynamic boundary conditions needed to describe the heart as a $\Delta V$ heart pump (heart cluster state machine) are clarified by giving examples of subdivided boundary conditions for the working principles of the muscle cell and subdivided boundary conditions for the working principles of the heart being a $\Delta V$ pump.

I The dynamic boundary conditions of a muscle cell as being a finite state machine, can be subdivided in boundary conditions and working principles as follows:

Ia the boundary conditions of chemical, electrical and mechanical ways of creating power and triggering the finite muscle state machines being parts of a conduction system in order to, in synchronized ways, achieve optimal order for the pumping- and regulating functions of the heart.

Ib the boundary condition of a connective tissue network around the muscle cells allowing firm constructions, elongating and shortening with enough space for the muscles being thicker at the muscular contraction.

Ic the boundary conditions of arranging muscle cells to create a four-chamber volume pump acting like a $\Delta V$-pump but serving to circulatory systems keeping them in an exact balance. Naturally, two and three chamber hearts will have other conditions.

II The dynamic boundary conditions of the heart working as a $\Delta V$-pump state machine are subdivided in boundary conditions and working principles as:

IIa The boundary conditions of surrounding tissues encapsulating a four-chamber volume with in- and outlets having functions and properties supporting the $\Delta V$ functions of the heart.

IIb. The boundary conditions of a movable $\Delta V$-piston, having valves, and outlet vessels, dividing an inner continuous volume of the heart into supplying and expelling volumes and also generating $\Delta V$ volumes arranged to create $\Delta V$ functions.

In traditional circulatory systems with ordinary pumps it is usually the speed of the pumps that controls both the inflow and outflow. That is not the case with the Dynamic Displacement pumps, the $\Delta V$-pumps. They are inherently controlled by the inflow. The $\Delta V$-volumes creates $\Delta V$-functions that determine the stroke length and in case of the heart also determine the sizes of the heart as a $\Delta V$-pump. This means that the $\Delta V$ heart pump has to be incorporated in a circulatory system to show or create its true pumping and regulating functions. In this way the dynamic boundary conditions controlling the venous return will have a very important role in controlling the cardiac output. The $\Delta V$ heart pump will, if the frequency and power are high enough, always try to pump away the blood that is coming through its inlet vessels. This has earlier not been fully understood. The main dynamic boundary conditions of circulatory system that are needed to support or being supported by the $\Delta V$-heart pump can be described as:

III Dynamic boundary conditions of the central venous volumes (e.g. pressure, flow, volumes, tensions of the larger veins including the pulmonary veins leading to the heart).

IV Dynamic boundary conditions of the peripheral venous volumes (e.g. the blood volume exchange and storage capacity of capacitance vessels).

V Dynamic boundary conditions of the central arterial volumes (e.g. pressure, flow, volumes, tensions of the larger arteries including the pulmonary arteries leaving the heart).

VI Dynamic boundary conditions of the peripheral arterial volumes (e.g. the variations of blood volumes needed to support different organs at different times and activity's controlling the flow rate in the transitional zones, and pressure drop to values of the venous pressures).

VII Dynamic boundary conditions of keeping the total blood volume, blood densities and viscosities.

VIII Dynamic boundary conditions for controlling heart rates and blood pressures.

With the heart presented as a $\Delta V$ heart pump it will be possible to modulate and simulate the natural circulatory system. The synergies between the functions of the heart and the functions of the circulatory systems will be better understood and will increase the demands of having answers to the questions when, where, how and why the heart does perform as it does. It will for example be very useful in medical treatments, intensive care and research.

In other words, each muscle cell must be arranged/configured such that it both fulfils the conditions for its own working regimen and also fulfils the requirements as a part of the structure building up the heart as a ΔV-pump. The working regimen creating power by shortening and thickening and the boundary conditions behind that are well known.

All experimental working models of the heart have under all circumstances been described with squeezing functions. This was obviously the case when the heart was supposed to do its pumping and regulating functions by external squeezing motions of the atria and ventricles in a rhythmic counter acting way. This is still close to 100% believed to be the true pumping functions among ordinary people and doctors in general.

With the new Magnetic Resonance Imaging technique (MRI) the opinion among leading researcher for the fourth time in history adopt the idea that the heart is close to be a constant volume pump pumping with the AV-plane.

It has during at least 200 years been known and generalized that heart muscle is built up by three layers. One outer layer with longitudinally twisted spiral fibres running counter clockwise from the AV-ring down towards Apex and returns as inner clockwise longitudinally twisted spiral fibres. In between a circular muscular layer is formatted. Finding the filling forces to the heart has always been a problem. In order to find these forces a few years ago the so called Ventricular Myocardial Band Theory was lounged to solve the mysterious filling of the heart. In that model the outer and inner layers are used to make a counter clockwise and a clockwise rotation of the heart by delayed contractions called a systolic ventricular filling. Thickening of the heart muscle was giving the pumping function. Very recently this theory was totally denied by anatomical specialist that had investigated the heart muscles in thin slices with electron microscopy. They found no layers that could slide against each other. They could verify the earlier known orientations of the muscle fibres and that the left ventricle also had strong circular orientated muscle cells in the centre of the muscle. That was not the case for the right ventricle.

The muscle cells way of working by shortening and thickening will generate problems once closed volumes as in the heart are made. The muscular cell volumes remain constant during its working states. This means that every working muscle cell because its thickening will have an impact on its neighbor cells and so forth. The volume geometry in the short axis view of the whole heart and the left ventricle in particular is more or less circular in shape. It means especially if the heart should do its pumping functions by squeezing pumping functions that every muscle cell have to interact in pushing, pulling and rearranging itself and neighbor cells in all directions on its way and thickening towards the center.

Nature has created a large spherical DeltaV-piston. This piston starts far below the AV-ring where the conical part of the ventricular outer contours proceed to a spherical form that finally is attached to the AV-ring. This formed spherical area is to a large extent covered by the auricles and their edges and generates together with the outflow tract of the Aorta and T. Pulmonalis the DeltaV-piston. The large area of the DeltaV-piston reduces the need for a long stroke length, reduces muscular obstructions to flow and creates DeltaV-volumes.

Organized muscle cells in a longitude clockwise outer "layer" and an inner longitude counterclockwise "layer" to form an X orientation, with a reinforcement circular oriented "layer" in between as a muscular crossing over (a bended 8) in the left ventricle, together with a complex network of trabeculae, generates longitude motions and a narrowing that can follow the outer contour set by the pericardial sac and its surroundings.

The muscles way of working by shortening and thickening will become a matter of packing and unpacking in a proper physiologic order. The thicker the muscular wall has to be the harder it will be to solve these tasks and finally the muscles will be an obstacle for the pumping and regulating functions of the heart.

Since the muscles volumes do not change neither as construction material nor as power source, building up and powering the atria, auricles or the ventricles. This means that the options to create pumping functions powered by the muscles are (FIG. 8):

1. Outer contour changes and thus outer volume changes
2. Constant outer contours with piston like motions of the AV-plane inside the heart
3. Constant outer contours with diaphragm pump like motions of the separating wall between the right and left halves rendering in reciprocating volume changes and pumping functions Nature has in ventricular systole made use of all three possibilities by creating (1, 2) the DeltaV-piston with external volume changes (DeltaV-volumes) in direct and indirect contact to the spherical DeltaV-piston.

Another external volume change, earlier not recognized, and also a part of the DeltaV-volumes are created by the motions of the outflow tract of Aorta and Pulmonalis.

A third external volume change is created as a result of the need for counter acting forces to the motions of the DeltaV-piston.

In a living being, the piston holds four valves and also the outlet vessels, Aorta and Pulmonalis. The whole construction, including the pericardial sac, is flexible and has to a certain extent elastic recoiling elements. The surroundings of the heart is also flexible except for the thoracic cage and the spinal cord. The strong attachment of the pericardial sac to the diaphragm muscle and hydraulic attachment to the thoracic wall makes the pericardial sac including the heart free to move in parallel with the thoracic wall during breathing, and have during the pumping action an important function as a resilient suspension keeping the total mass inside the pericardial sac in motion at the end of ventricular contraction. The resilient suspension at Apex will reduce the stroke length of the DeltaV-piston but can together with other recoiling forces, static and dynamic forces, power the hydraulic return of the DeltaV-piston by the DeltaV-function. The hydraulic and mechanical attachment of the base of the heart and the inlet vessels to the heart, will see to that this area, opposite to the apical area, will be kept in place, both during atria- and auricle contraction as well as during ventricle contraction.

The diaphragm pumping motions (3) of especially the ventricular septum are of great diagnostic importance in visualizing the status of the hearts pumping and regulating functions. As discussed above, the muscles way of thickening should not be interpreted as synonymous with a volume displacement. This means that the contraction of the ventricular septum as a shorter and thicker unit does not change the volumes between the ventricle volumes. It is just a motion that can do that. Since usually the systolic and diastolic pressures are higher at the left side of the heart, the left ventricle, including the ventricular septum, will have a spherical shape. This results in that the muscular cells is oriented to withstand the pressure gradients towards the right ventricle during the ventricles contractions. This means that the muscle mass of inter ventricular septum will orient its thickening towards the left ventricular lumen. In other words, it will be the motions of the surface area next to the right ventricular lumen that change the volumes between the two ventricles. The ventricular septum is regarded to have two kinds of motions. One that is in parallel with the diaphragm resilient movements that does not change the volume inside the left ventricle but to a certain extent the volume in the right ventricle. The other motion of the ventricular septum interacts between the ventricles by increasing the stroke volume at one side while decreasing the stroke volume on the other side. This will give a very effective double regulating function that under normal functions in septum will keep the pressure over the pulmonary circulatory system at low, normal levels.

The longitude motion of the inter ventricular septum contributes to a third volume exchange, earlier not known, between the right and left ventricles. This volume is an internal DeltaV-volume added to the external DeltaV-volume of the outflow tract of aorta and indirect through the outflow tract of Pulmonalis. The volume is generated as in the rest part of the left ventricle by the spherical connection of the ventricular septum to the AV-ring. This means that the left ventricle in making the internal DeltaV-volume, every beat will "steal" from the stroke volume of the right ventricle, a volume that will be returned during the hydraulic return of the DeltaV-piston. This can easily be seen on the graphical user interface, according to the present invention, aimed at flow characteristics.

Atria contraction may be regarded as being a booster, generating an increased stroke length. The large area covered with double folded auricles and their sharp muscular edges can be withdrawn by contraction. This generates instantly a situation where a total vacuum would appear if the surroundings would not collapse or if the DeltaV-piston would not be lifted up. The later will occur since an upward motion of the DeltaV-piston and a thinning out of the muscular walls will result in equal volume displacement above the DeltaV-piston. This will result in a minimum of less change in speed of all masses inside, outside to and from the heart. At high flow and heart rates, and thus strong forces behind the DeltaV-function, the atrial contraction, except as a result of the conduction system, will have fewer effects on the stroke volume. Whereas in heart failure it can have life sustaining effects.

With the above-described dynamic boundary conditions millions of vectors will cooperate and build up the $\Delta V$ heart pump and its functions having shapes, structures and functions that the real heart in fact has.

Thus, a logic state diagram of the heart being a $\Delta V$ heart pump with the above mentioned dynamic boundary conditions can be followed and described with practical event markers seen in different kinds of investigation methods.

Here is the event markers set following seven main logical states or phases that easily can be seen in Echocardiography. For practical reasons describing the fundamental mechanics behind the $\Delta V$-heart pump concept these event markers are set by events related to the left ventricle. Of course the same events related to the right ventricle should be taken in account in investigating methods where they can be found, though the interaction between the right and left heart is of great importance for the $\Delta V$-heart pump concept. The difference in intensities and timing may serve as good and sharp diagnostic tools. Every change in e.g. timing between these major states will have an impact of the following state and serve as diagnostic tools telling when, where, and why the heart is pumping as it does.

Figure 1:
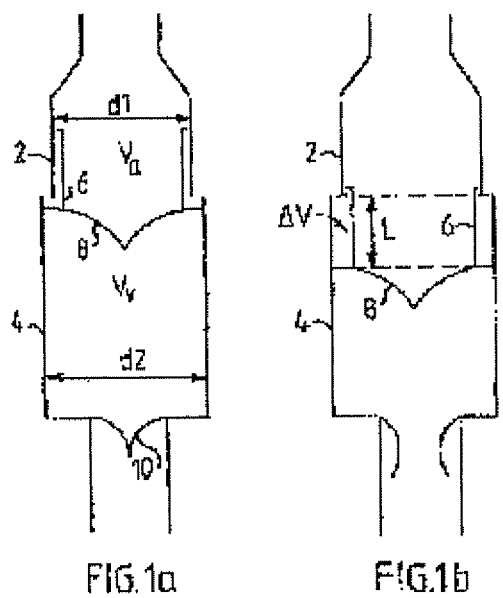
Figure 2:
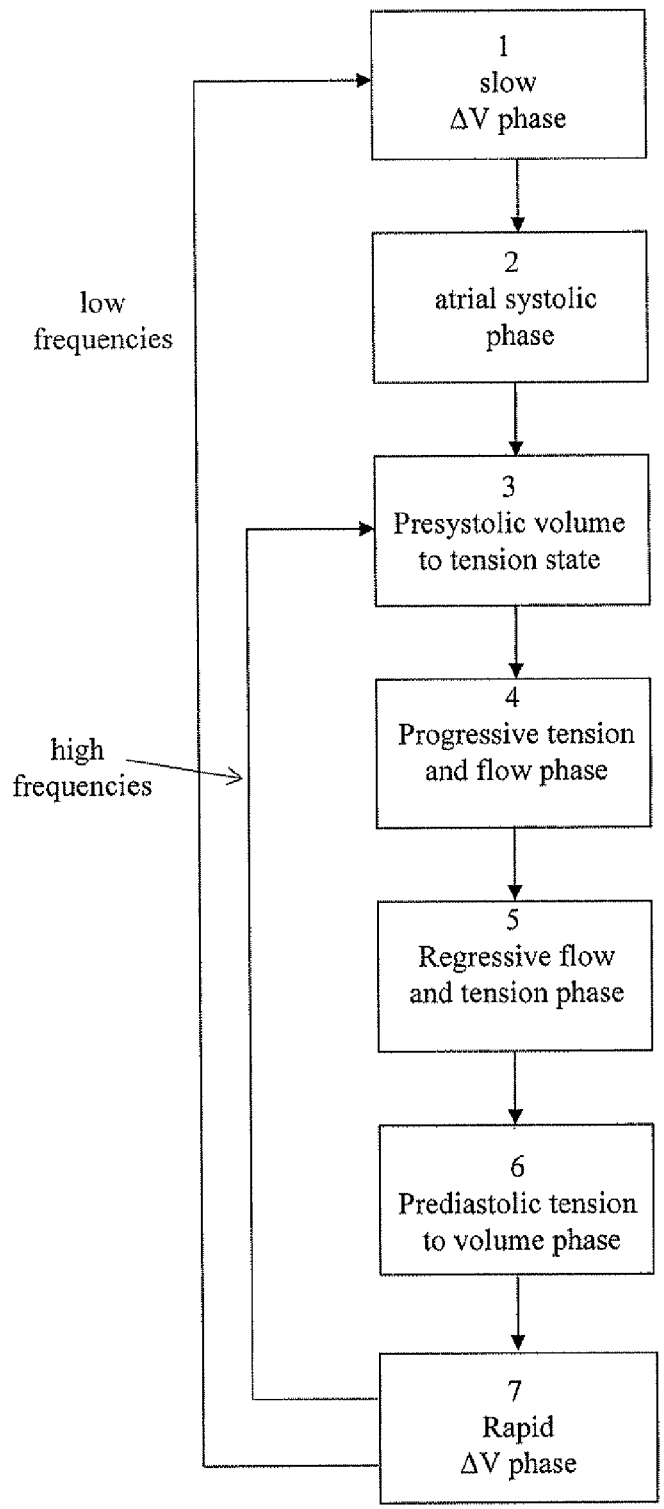
FIG. 2 is an example of a logical state diagram of the heart being a ΔV-pump.
Figure 3:
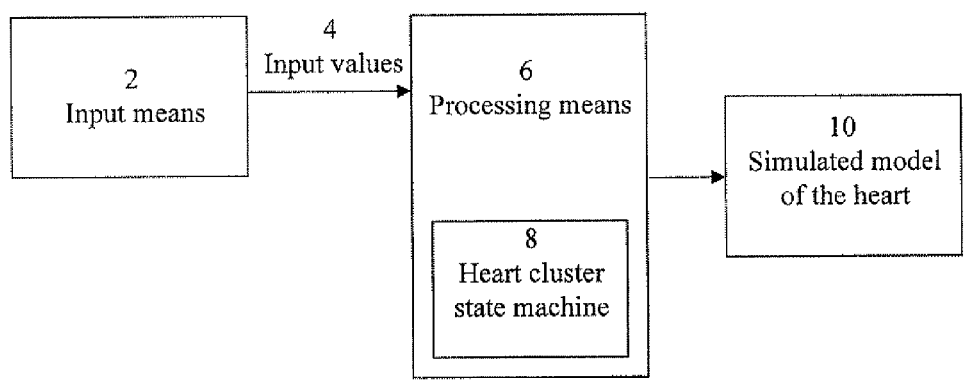
FIG. 3 is an example of a block diagram that schematically illustrates the ΔV-heart pump and the circulatory system according to the present invention.

With references to FIG. 2 the different states will now be described in detail.
State 1
Slow $\Delta V$ Phase.

This phase was earlier referred to as the slow filling phase. But in this context, where the heart works as a $\Delta V$-pump, the "slow $\Delta V$-phase" is more relevant. It is a direct continuation of the rapid $\Delta V$ phase, the returning movement of the $\Delta V$-piston. During slow flow and low rates the slow $\Delta V$ phase is relatively long.

During this phase the muscle cells of both the atrias and the ventricles, as well as the ventricular septum, are totally relaxed. The left and right halves of the heart may principally be regarded as common volumes inside the pericardium. This results in that the right and left half of the heart, respectively, forms, together with the incoming vessels, compliance volumes. The energy in the incoming flows to the left and right atria result in that the volume of the heart primarily increases in the vicinity where the $\Delta V$-piston moves. This generates energy to the $\Delta V$-functions resulting in that the $\Delta V$-piston changes its shape and position and also generates stretching forces to the ring of annulus fibrosis. The energy in the incoming flows is transferred to both ventricles essentially without being disturbed by the ventricular septum.

The total volume of the heart is depending on the heart frequency and inflow.

The size of the $\Delta V$-pump will be set during this state.

The pericardium and its environment are the main limitations to the possible volume expansion of the heart. During this phase the static forces in the inflowing blood are the most prominent forces. Those surfaces forming the indirect $\Delta V$-volumes (mostly the auricles of the atria) do not contribute during this phase to any net forces to press the $\Delta V$-piston in the direction to the top of the heart. It is mainly the direct $\Delta V$-volumes formed by the enlargements of the heart in connections to the $\Delta V$-piston and the outgoing vessels that performs that action. The egg-like shape of the heart results in that the net forces and the motion of the $\Delta V$-piston towards the top of the heart are limited. The $\Delta V$-piston will enter into a neutral balanced position. This will limit the stroke length of the $\Delta V$-piston, but the widening of the $\Delta V$-piston encompasses larger volumes.

Thus, the heart as a $\Delta V$-pump adapts its size and form in relation to the incoming flow and heart rate.

The filling pressures of the right and left heart halves, respectively, determine the pressure gradient over the ventricular septum. The pressure gradient determines the shapes and positions of the ventricular septum between the right and left ventricles.

This state and state 2 and 3 form, together with the previous state (which is state 7), the prerequisite for the double regulating function of the ventricular septum.
State 2
Atrial Systolic Phase.

According to established teaching the atrial systolic contraction and its associated ECG-signal was the starting point when describing the heart's pumping function. The time between two atrial contraction was denoted a heart period or a heart cycle.

The discovery that the heart works as a $\Delta V$-pump implies that its pumping and controlling functions are controlled of the incoming flow which in turn implies that a description of a heart cycle must start with the slow $\Delta V$ phase. The results of the atrial systolic phase depends upon many different parameters and may under certain circumstances result in that the atrial contractions do not add anything to the heart's pumping function, whereas during other circumstances it gives life-sustaining contribution.

During low rates and reduced momentum behind the $\Delta V$-functions in state 7, the atrial contractions contribute to lift the $\Delta V$-piston above its neutral position in state 1. The atrial contraction is a rapid activity. The hydraulic attachments of the atria and its auricles to the pericardia and to the spherical part of the $\Delta V$ piston, create during atrial contractions a withdrawal sliding motion on the top of the relaxed and formable ΔV piston and along the pericardial sac. This will create a hydraulic power that forces the ΔV piston in the direction to the top of the heart. During the contraction there will be a redistribution of the blood volume between the atrias and ventricles at a minimum of external and internal acceleration of masses. The pulling of the ΔV piston to the top of the heart is favoured by quick atrial contractions because then the momentum against motion of the inner and outer masses are large. Since the total volume of the heart is fairly constant during the atrial contraction the sliding motions of the ΔV-piston against the pericardial sac only results in a redistribution of blood between the atria and the ventricles. The more or less only areas that can generate a need of external inflow volumes during atrial systole are the outflow tracts of T-pulmonalis and Aorta. These areas can generate both direct and indirect ΔV-volumes. During atrial contraction there is an inflow to the right atria but usually there is a small backflow from the left atria. This is most likely depending of small compliance volumes in the pulmonary veins and the fact that the left auricle is squeezed between the ΔV-piston and the lung veins and thus widening the veins during a withdrawal contraction. During large flows and high heart rates, with large momentum behind the rapid return of the ΔV-piston, the flow dynamics behind the ΔV-functions force the ΔV-piston to passes its neutral position. The role of the slow ΔV phase bringing the heart to a full size ΔV-pump is reduced, due to large dynamic forces and a background of static forces that can keep the heart at full size. The atrial contraction can more or less not contribute to any further motion of the ΔV-piston to the heart base.

During small ΔV-piston movements, caused by a lot of reasons, low momentum behind the returning motions of the ΔV-piston, phase 6, the atrial contraction can contribute, up to 60%, of the stroke volume by lifting the ΔV-piston to the base of the heart.

The mechanism behind the dramatic differences regarding the importance of the atrial contraction during high and low flows and rates, respectively, and during heart failure, has never had any mechanical explanations before. That is also true for the role that the auricles plays for the pumping function. The heart as a ΔV-pump gives an important mechanical explanation of the atrial contraction and the auricles role for the pumping function.

It also explains why the inflow to the heart can continue despite ongoing atrial contractions.

After atrial systole follows the ventricular systolic expelling phase, here divided in three states. Since the pressure during this phase usually is much higher in the left ventricle, the left ventricle can be looked upon being a separate ΔV-pump working in collaboration with the ΔV heart pump.

State 3
Presystolic Volume to Tension Phase

After the atrial contraction the conduction system, after a certain AV-delay, in synchronised orders, starts to depolarise muscle cells in the ventricles. During state 3 (earlier called the iso-volumetric phase) the muscle not only has to create power to the heart but also has to, being the construction material, strengthen the parts of the heart that within the next time interval will be exerted by high forces.

The ventricular septum, the apical and conical parts of the ventricles and the papillary muscles will be activated first. Within a few milliseconds thereafter the initiation is spread to the rest of the heart, that means the spherical muscular sphincter like parts of the ventricles, i.e. the ΔV-piston. The way of activation of the ventricles may be regarded as a "soft start", and is useful during later phases when the ΔV-piston starts its relaxation and returning movements.

The initiation follows a pattern that optimises the presumptions of the ΔV-piston movement towards apex. Interventricular septum starts stabilizing in order to withstand the pressure gradients between the left and right ventricles. The left ventricle format with interventricular septum and its connections to the AV-ring and outflow tract of Aorta, as a direct continuation of its external shape, an internal sector of the ΔV-piston, that will interact with the volumes in the right ventricle.

The started activation of the ventricular heart muscle results in increased tensions in the heart muscles. This results in force vectors that by the construction both want to narrow the gap between the ΔV-piston and the apical-diaphragmal region of the heart and also to generate pressure gradients towards the enclosed blood volumes. The tension will create a motion in the fields where resistant against motion is lowest. The hydraulic attachments of the heart to the pericardia and the surrounding tissues creates, as is the case during the atrial contraction, sliding motions of the ventricular muscles along the pericardial sac due to that the resistance to motion of the inside and outside masses are large. An internal redistribution is obtained of the blood volume between the atria and the ventricles but in the reverse direction, resulting in closing of the valves with virtually no back-flow.

A continuing down pulling of the peripheral area of the ΔV-piston, that has a firm connection to the AV-ring and hydraulic connections to the auricles and the pericardia has a concave form in connections to the muscle mass and the enclosed blood volume. This bended form works like a first class levers (FIG. 8) and can, by bending and pulling, generate and withstand strong force gradients. Of course this needs extra strong reinforcements of circular oriented muscular fibres in the left ventricle were the pressure gradients over the ventricular wall is much higher.

It is within this bended area that the volume exchanges per stroke length unit will be greatest and it is also here and at the outflow tract of Aorta and T. Pulmonalis that the direct and indirect ΔV-volumes are generated.

In the beginning of the state the right and left ventricles are regarded as one single volume with communicating volumes to the atria and the inflow vessels. During the pull-down of the ΔV-piston and closing of the valves the pressures inside the ventricles increase. The motions of the ventricular septum now reflect what kinds of relationship there were between the static and the dynamic pressures at each side of the ventricular septum at the end of the atrial contraction, and also how the ventricular muscle is activated.

At the end of state 3 the volume redistributions have made the ΔV-piston, the AV-valves and the ventricular septum and the internal sector of the ΔV piston to start to assume the shapes and tensions they need to withstand the pressure gradients that are generated in reaching the pressures that will start an outflow from the right and left ventricles. During normal circumstances all these adaptations occur, in balance with outer resistance of fast volume changes and also concerning the motion of the ΔV-piston in balance with inner fast volume changes. Most of the inner volume changes as results of the sliding motions of the ΔV-piston are done (FIG. 8), by internal redistributions of blood volumes. The inflow to the atria can continue, especially at high flow rates, due to their relaxation especially in the areas where the auricles are covering the convex muscular parts of the ΔV-piston and in the areas around the aortic and pulmonary roots where the auricles are filling up volumes that are difficult to access.

State 3 includes many important event and time markers for the heart being a ΔV-pump and the ventricular septum being a regulator for the flow to the pulmonary and to the main circulatory system. With marking points at different locations of the ventricular septum, it can serve as a large and sensitive pressure membrane sensing the on-going activities giving lot of informations about the performance of the heart and the circulatory system. This event can also be monitored by more simple registration method e.g. Apex cardiogram.

State 4

Progressive Tension and Flow Phase.

Phase 4 starts as an index mark with the opening of the aortic valve and ends as a marker on top of the aortic outflow. During this phase the motion of the ΔV-piston generates a progressive tension and flow out and into the heart. The pressure is normally much higher in the left ventricle. This results in that the ventricular septum mainly assumes the same shapes as the other parts of the left ventricle. If the systolic shapes and positions deviate from the shapes and positions before the ventricular contractions, a volume adaptation takes place between the ventricles.

As a direct continuation of state 3 the spherical ΔV-piston will create both direct and indirect ΔV-volumes. These volumes, due to external resistance and recoiling forces and increasing blood pressure inside these volumes, will give a net increase of the pressure gradients over the areas producing the ΔV-volumes.

The acceleration of a mass demands power and energy. The masses to be accelerated comprise all tissues in direct and indirect connections to the motion of the ΔV-piston. These tissues are, all blood in the heart and in the vessels entering or leaving the heart, the heart muscle itself and the masses in the heart's environment. Furthermore, energy must be added for internal and external tension and recoiling forces, and friction losses, as for example created by motions of the Aorta and T. Pulmonalis and twisting torsions of the heart.

During phase 4 larger counter forces are required in order to pull the ΔV-piston towards apex. Due to that and the hydraulic attachments of the heart to the pericardial sac that in turn is hydraulically attached to the chest wall, an increased up-movement takes place of the conical part of the ventricular cylinder in parallel with the chest wall (FIG. 8). The phenomena can be mimicked with a vacuum cup that can slide on a slippery surface with forces parallel to the surface but give a high resistance to right angel forces.

Nature has fixated the pericardial sac with strong connected tissues to the diaphragm muscle but not to sternum, were the sac more or less is fixated by a hydraulic coupling. This arrangement avoids problems concerning the breathing mechanism.

The fixation of the pericardial sac, in this way renders the apical diaphragma region of the pericardial sac to act as a resilient suspension that results in a bending and lifting of Apex and the diaphragm against the chest wall. This suspension will more or less take care of all the counteracting forces that the ΔV-piston creates. Most of the counteracting resistant and recoiling forces are generated outside the common ΔV-piston by the creation of the ΔV-volumes and pulling and twisting the Aorta and T. Pulmonale. The counteracting forces between the ΔV-piston and the diaphragm area want to separate these areas in both directions. These events and energy will be regained to the pumping functions in the following phases. At high compliance and low resistance this state will be longer than at low compliance and high resistance. This may be a good diagnostic tool.

By performing measurements during this phase with even simple methods or devices like pulse pletysmography e.g Apex cardiogram and referring these data to the heart being a ΔV heart pump will in many cases give enough information about the hearts pumping and regulating functions within a specific circulatory system.

State 5

Regressive Flow and Tension Phase

This phase is in a direct continuation of phase 4 and ends as a marker with the closing of the aortic valve. During this phase both flow and tension starts to decline in the left ventricle that can be looked upon being a separate ΔV-pump working in collaboration with the ΔV heart pump. After phase 4 the declining movements of the ΔV-piston starts. The ΔV-volumes will still be formatted though the indirect ΔV-volumes can be refilled by inflow to the atria and auricles. The twisting of the Aorta and Pulmonalis continue as long as there will be a net motion along the thoracic cage in the direction towards apex. The flow out through the Aorta continues as long as there is a common muscular contraction that can withstand the pressure gradients over the left ventricular walls that can be done by a first-levers function in the muscular part of the ΔV-piston. This part of the ΔV-piston and the diaphragm part of the left ventricle has external forces that together with the pressure inside the ventricle want to separate these areas from each other.

During the end of phase 5 the counter forces above the ΔV-piston decline. The reasons for that are partly that the acceleration of the masses has stopped and partly that the compliance volumes in the incoming veins to the atria and the indirect ΔV-volumes especially located in the auricles have started to be refilled. The ventricles, looked as solid units, can start, because of stronger recoiling forces in the diaphragm area, to return to the neutral position this area had before phase 3. Due to the mechanical coupling this returning movement also results in a relative movement of the ΔV-piston, giving possibilities for continuous inflow into the atrial volumes despite that the real movement between the ΔV-piston and Apex declines and stops. In addition there is a declining pressure and flow in Aorta and in T. Pulmonalis which result in that their diameters decrease which in turn through their contact to the atria and auricles give room for continuous inflow into the atrial cylinder. The relative movement, but also the real movement of the ΔV-piston, is most pronounced in the region of the outflow tract of T. Pulmonalis.

The ongoing inflow above the ΔV-piston and the decreasing outflow from the heart will cross each other during this phase, which means that the heart will have its smallest total volume before the end of ventricular systole.

By performing measurements during this phase with even simple methods like pulse plethysmography units e.g. Apex cardiogram and referring these data to the heart being a ΔV heart pump will in many cases give enough information about the heart's pumping and regulating functions within a specific circulatory system.

This phase stops for practical reasons with the closing of the aorta valves but is in a middle of an ongoing process, further described under state 6.

State 6

Prediastolic Tension to Volume Phase

This phase was earlier called the isovolumetric diastolic phase.

This phase has a mechanical action that is running in a reverse way compared to state 3. That means that in order to release the pressure gradients in this described region, the left ventricle, there has to be an increase of the left ventricular volume. That can be done without disturbing any ongoing inlet flow to the heart and at higher heart rates and minute volumes also leave possibilities for ongoing outlet flow. The ongoing process in phase 5 with decreasing pressure gradients to the surroundings of the heart are, as earlier described, concentrated to the muscular parts of the ΔV-piston and the outflow tract of Aorta and T. Pulmonalis. Furthermore, these areas together with the areas in close connections to the diaphragm, which happens to be a part of the left ventricle, have contracting recoiling forces that want to separate these areas from each other through elongation and sliding motions of the ventricular walls along the thoracic cage. This surface of the heart also describes the longest distance between the ΔV-piston and Apex and has a very strong convex attachment of the ventricular muscles to the AV-ring and the sharp bend of T. Pulmonalis. This part of the ΔV-piston is well covered by the left and right auricles and need a strong support of muscle power. When that support goes down, the two areas, the ΔV-piston and diaphragm area start to be separated. This will both lead to a decrease in tension leading to internal redistributions of volumes and finally open the tricuspid and mitral valves. This event can also be monitored by more simple registration method e.g. Apex cardiogram.

State 7

Rapid ΔV-Phase.

The rapid diastolic returning movement of the ΔV-piston is a direct continuation of phase 6. An adapted relaxation means that stored energy in the surroundings, the twisting of the heart, can be released in a way that in optimal ways can bring the ΔV-piston back towards the top of the heart. The adapted relaxation creates a total release of the recoiling forces that wanted to separate the total ΔV-piston from the diaphragm area. This will add energy to the inflowing blood in the direction towards apex. Static and dynamic forces of the inflowing blood will exert a pressure on the areas that has created the ΔV-volumes, that means the ΔV-piston, and will create, by moving the ΔV-piston, a refilling of those areas. The movement of the ΔV-piston also creates a redistribution of blood between the auricles, atria and the ventricles and also in an early stage between the ventricles by a forth and back going motion of the interventricular septum. The enhanced dynamic forces in the directions to apex will be reversed by the ΔV-volumes (direct and indirect ΔV-volumes) that finally absorb the static and dynamic forces by filling and pressing the ΔV-piston towards the top of the heart. This action is referred to as the ΔV-function and will give the ΔV-piston a rapid diastolic return and dynamic forces behind the valves that together with the flow paradox will close the valves with no back flow. The return of the ΔV-piston will result in a thinning out of the left ventricular muscle, a motion that inside the heart will look like an internal peristaltic expansion wave front running from the ΔV-piston towards Apex.

This event can also be monitored by more simple registration method e.g. Apex cardiogram.

At low frequencies the ΔV-piston performs an overshoot and a recoiling movement. This is an effect of the forces of inertia that the blood has acquired and stored in an expanding wave behind the valves pushing the ΔV-piston in the direction of the direct and indirect ΔV-volumes. Once the dynamic forces have ceased the static forces will dominate and bring the ΔV-piston to a neutral expanding position, state 1.

At higher flows and frequencies the slow ΔV phase (state 1), the atrial systolic phase (state 2) and to a certain degree also a part of the early part of the presystolic volume to tension phase (state 3) in flow dynamics point of way will be overruled. The fast diastolic return of the ΔV-piston carried by an expanding wave with a lot of dynamic energy is followed more or less directly by the ventricular contraction (state 3). This is schematically illustrated in the state diagram of FIG. 2.

The strong expanding wave and the force of inertia will bring the ΔV-piston even higher up to the heart top than the atrial systole can do.

At high flow rates and frequencies ΔV-pumps due to the inertia of the in and outgoing fluid including the fluid in the pump will start to generate a more or less continuous outflow with no need of outlet valves. Still the inlet flow will create the ΔV-functions. The ΔV-pumps start to increase their stroke volumes above that can be calculated by the piston area times the stroke length.

These circumstances applied on the ΔV heart pump will during high inflow rate and high frequencies due to both static and dynamic forces in the blood flow keep the volumes of the heart above the ΔV-piston in a more or less full size at the time when the rapid ΔV phase starts. The volumes of the heart below the ΔV-piston will at the same time be low because the outflow inertia. This will create an increase of the ejection fraction that earlier never has been understood.

With the insight that the heart appears in its pumping function more like a piston pump, or a pressure and suction pump, and even more precise as a DeltaV-heart pump, with abilities to be controlled by inflow, it is now possible to relate all physiologic activities concerning the heart and circulatory system in state diagrams. The interactions between the states for the total outcome of the pumping and regulating functions of the heart may with a state machine interface, according to the present invention, in real time, beat by beat, be monitored and analyzed. Furthermore, impacts of e.g. in- and outflow, inotropic and chronotropic effects, normal and abnormal muscular functions, medical and surgical interventions and so forth, may also be studied.

For better understanding a working principle of a DeltaV-heart pump it can be mimicked with a two stroke combusting car engine. This machine can e.g. be referred to as a cluster state machine of a displacement pump having a piston, crank, crankshaft, flying wheel, inlet and outlet valves, and a fuel and ignition state machine. The combusting engine can for example be described with a four state diagram such as progressive and regressive forwards and backwards movements of a piston. A fuel and ignition state machine, supporting the energy, is liked to the displacement pump. The combustion creates power that is transformed by the piston, crank and the crankshaft to mechanical work and to the flying wheel as stored energy to be used for the return of the piston and compression of an air and petrol mixture. Even though the two state machines are linked together, it is easy to find out, knowing the principles behind the constructions, if there is a bad or good performance of the fuel and ignition state machine or a break down in the displacement pump, because the displacement pump, in this example, does not change its construction variables during running.

The heart as a pump is made and powered by the muscle cells. In comparison with the combusting engine, the DeltaV-pump has no mechanical means to bring the piston back. Instead the DeltaV-pump uses the incompressible masses like the muscles and blood as piston and crankshaft and the DeltaV-function as a flying wheel, absorbing energy needed for the return of the DeltaV-piston.

The fuel and ignition state machine in the combusting machine is comparable with the finite muscle cell state machines in the DeltaV-heart pump. The working mode of a single muscle cell and as a cynsytium of cells will, in contrast to the combusting engine, have a great impact on the working regimen of the DeltaV-pump. This means that normal activity changes like changes in chronotropi and inotropi and pathologic changes like, conduction faults, ischemia, infarctions etc. and a mix of them, can jeopardize the mechanical functions and reduce the pumping and regulating functions though there is enough power left.

The state machine interface system according to the present invention will now be described in detail in the following.

With a state machine interface system it is now possible, at all flow and frequencies, in real time, to find and transform physiological activities in and around the heart and circulatory system and transform these into different states of the heart cycle, wherein said different states graphically are adapted to be organized and presented by the interface system at a graphical user interface such that the temporal relation between the different states are illustrated as graphic state diagrams of the heart's pumping and regulating functions even down to cellular level.

The graphical user interface will now be described by exemplary graphical state diagrams presenting the pumping and regulating functions of the heart.

The state machine interface system (available under the registered trademark GrippingHeart® graphic lab), (FIG. 6), is adapted to store, or directly on-line with state machine algorithms, transform input data to states and with graphical user interface algorithms present various types of state diagrams. Input data may be collected data from various investigating methods and target areas inside and outside the heart. Velocity changes can preferably be used as trigging points from hydraulic and mechanical activities detected by various investigating methods. Trigging points can manually and/or automatically be accepted to be transformed to states by the state machine algorithms and finally by the graphic user interface algorithms be transformed automatically on-line, as various types of state diagrams.

Signals to be used to create trigging points may vary in quality depending on investing tool and investigated areas. With fewer trigging points a less detailed state diagram can be presented, but it still fits within a more detailed state diagram. Possibly missed states may be added during the next heart beat at the same or another investigated areas and investigating tools. This means further that different investigating tools and investigated sites can be mixed to generate a more detailed state diagram even down to the micro level of the heart muscle cell and the conduction system.

According to the present invention, two different types of state diagrams can be classified as e.g. purely time-related state diagrams and user-specific state diagrams (FIGS. 4 and 5, respectively).

Time-Related State Diagrams

Time-related state diagrams are state diagrams that only have time-related states that e.g. may be presented as circles and/or bars on the graphical user interface (FIG. 4).

Since all structures inside the pericardial sac including the heart's own internal circulatory system are theoretically incompressible, a single muscle cell contraction would have an impact on the whole enclosed volume inside the pericardial sac, to be further transformed to the surroundings of the heart, as well as to inlet and outlet vessels, coronary and possibly bypass arteries. Due to that, time-related state diagrams may be determined by trigging points picked up at any point that have a relation to the pumping and regulating functions of the heart.

State diagrams monitored from the surroundings of the heart will more or less be referred to the functions of the left ventricle. One exception might be the motion of the Apical-Diaphragm part that most probably to some extent reflects the inflow to the right ventricle. An advantageous device to use for picking up and generate trigging points will be an accelerometer as a velocity sensor attached on the surface of a body close to apex or larger arteries. This sensor and other sensors like oximeters and blood pressure sensors, can, beat by beat, in real time, absorb enough data to generate complete or partly complete state diagrams. These diagrams may be evaluated by man and/or automatically be linked (e.g. via telemedicine) to local and or global systems that interact with preferred state diagrams.

Time-related state diagrams demonstrate on-line variations and shifts during various flow and frequencies under normal or pathological circumstances, with or without medications, before, under and after a training period etc. In many cases one outer ring of a circular diagram showing the state diagram of the left ventricle will give enough information to serve as a final diagnostic tool for manual and/or automatic interpretation, see FIG. 4.

Other on-line observations like blood pressure monitoring, breathing, chest pains, lactose's feelings and warning signals can be added and simultaneously be presented and compared with the state diagram. This very simple state diagram compared with local and or global systems can in many cases be enough to describe the actual functions of the heart. Since it is known that the coronary flow is reduced to zero during ventricular systole, the time-related state diagram also can be used as an optimizing, diagnostic and warning system in relation to e.g. the coronary flow. The time-related state diagram is very easy to produce, analyze and communicate. It can be used by individuals, with for instance accelerometers as investigating tools, interested in following up medication and or training effects. It is very suitable for public use and telemedicine.

Internal registering methods like echocardiography can produce trigging points simultaneously from both the right and left side of the heart and thus two interacting time-related state diagrams can be presented. This is illustrated in FIG. 4, where the outer ring represents the left side of the heart, and the inner ring represents the right side of the heart.

The difference in timing between the left and right state diagrams at rest and during different flow, pressure, frequencies, medications etc. will be of great value for evaluations of the hearts functions. Since there are no needs for precise registrations, this will be an easy documentation even at high workloads, e.g. working tests. Internal devices, like pacemakers, may easily, with various types of sensors, pick up physiological activities, and by the state machine interface system transform these to time-related or user-specific state diagrams as to analyze, communicate, regulate and optimize medical treatments and the variables of the device to create e.g. efficient heart activities in relations to coronary flow.

User-Specific State Diagrams

User-specific state diagrams are time-related state diagrams with additional related variables.

The most direct way in determining and analyzing the hearts pumping and regulating functions in a quality and a quantitative point of view would be to analyze and quantify the motions of the outer contours around the heart and inside the heart that separate the internal volumes from each others as described above (FIG. 8). This working model "separates" the working regimen of the muscle state machines from the working regimen of the DeltaV-pump. In this way it will be much easier to understand what kind of factors and forces that have impacts on the motions of these areas. Today there are no investigation methods that are focusing their measurements and algorithms on these facts, since the general belief is that the heart is pumping with squeezing motions. One of the aims with GrippingHeart® graphic lab is to create algorithms to detect, use, calculate and display the functions of the heart referring to the above described outer contours.

Local heart muscles disturbances like infarcted and ischemic areas, conduction faults leading to dyskinetic functions can with new invention methods like Tissue Velocity Imaging (TVI) display these areas even at high frequencies. Strain Rate Imaging (SRI) is another method measuring deformation velocities in longitudinal directions (lengthening and shortening) and or in lateral directions (thinning and thickening). The latter method is good in finding regional defects in the muscles but too slow and makes artifacts at high heart rates These two investigating methods are now used in ultrasound investigating devices. They may present physiological events during a heart cycle as velocity and motion events. The TVI signals are quite resistant to noise and are suitable input signals for automatic detections of trigging points, to be used as input values to the state machine interface system according to the present invention, at any site in both the right and left ventricle.

This means that this investigating method with the graphical user interface in real time and on-line can produce states that in a graphical organized ways may present both time-related (FIG. 4) and user-specific state diagrams (FIG. 5) at different sites, flow and frequencies. The diagrams can serve as final documentations and can manually and or automatically be analyzed with local and or global systems. The results can easy be compared with the same or other investigating methods and its states are easy to discuss and communicate e.g. via telemedicine. The graphical presentations broaden the information about the pumping and regulating functions of the heart and dramatically reduce the operators work. Its easy way of working can be used for a fast scanning of e.g. school classes and sports team. Every result may be stored, compared or checked on-line with local and or global systems. The graphical user interface may include specific algorithms adapted for use of cheaper echo transducers as sensor device.

By adding or directly recording different kinds of variables like stroke length of the DeltaV-piston, movements of the ventricular septum movements of the diaphragm surface, flow and pressure, medication etc, together with a time-related state diagram, a user-specific state diagram, can be created and analyzed.

Recording methods like Echocardiography, Spin CT, MRI and gamma cameras can all be used to depict motions of the total heart and structures inside the heart including flow to and from the heart and the hearts own circulatory system. They can also to some extent display pressures. They can all present motions of the heart by 2D sector scanning or frames with frame rates at "normal width" at approximately 200, 60, 30 frame rates/minute, respectively. They are all objects for making 3D visualizations with a focus on the squeezing motions of the muscles. These methods have drawbacks in that they require high computer capacity, lower the frame rates and make low resolutions and inexact calculations.

By "separating" the working regimen of the finite muscle state machines from the working regimen of the DeltaV-pump as descried above (FIG. 8), the smooth surfaces, (except the surface of Ventricular septum) that can create pumping and regulating functions will be "free". It is now possible with a narrow sector or even with an echo beam by mapping the described surfaces with user-specific state diagrams to calculate volume and volume changes inside and outside the heart during the whole state diagram. Volumes like DeltaV volumes, resilient suspension volumes, in and outflow volumes, volume to tension and tension to volumes, regulating volumes, regurgitation volumes, and other volume changes due to mal functions of the heart can be quantified and displayed.

The mapping, being a part of the state machine interface system, can be produced with the same investigating tool as TVI and SRI and thus can this diagram, displayed as e.g. volume shifts over time, be displayed as being a part of the presentation of the regional muscular functions or the other way around. This can be the ultimate method to display all kinds of functions and mal functions of the heart.

The mechanical state diagram of the heart results in hydraulic work both into and out of the heart. The compliance and resistance of the vessels and to a certain extent their own activities will create distortions. That will change the possibilities of finding the trigging points that close to the heart generate the mechanical state diagrams. Time-related state diagrams close to the heart, in combination with time-related state diagrams over larger arteries (e.g. accelerometers) and even at capillary levels (e.g. oxymeters), can be compared at rest and also during work. This may generate individually related transforming values, calculated trigging points, that can be of diagnostic value concerning the circulatory system, and also render to new individual specific trigging points that can depict the functions of the heart.

The state machine interface system (GrippingHeart® graphic lab) may, except for being a diagnostic tool, also be a research tool and serve as a supporting link for local and/or global systems and databases.

Thus, FIGS. 4 and 5 illustrate two examples of graphical user interfaces according to the present invention where the heart cycle states are graphically presented in a circle diagram having sectors representing the different states and that the size of each sector depends upon the duration of the respective state. In the figures may be included numbers indicating the duration (in ms) of each state. An inner part of each sector represents states of the right heart half and an outer part of each sector represents states of the left heart half.

As an alternative (FIG. 9) the heart cycle states are graphically presented in one or many bar graphs divided into parts, each representing the different states, and that the size of each part depends upon the duration of the respective state. In that case one bar graph represents states of the right heart half and another bar graph represents the states of the left heart half.

Further alternative geometrical illustrations are naturally possible within the scope of the present invention as defined by the claims.

To enable a user to easily identify relevant information from the displayed state diagram each presented heart cycle state may have a predetermined colour, or pattern, in order to clearly distinguish the states from each other. Furthermore, auxiliary information related to each displayed heart cycle state may be displayed in connection to the displayed information.

FIG. 7 is a schematic block diagram generally illustrating the functional relationships between the state machine interface system according to the present invention and systems/devices interacting with the interface system as described in detail above.

The state machine interface system, as described herein, is included in a heart state machine analyzer and/or simulator, which preferably is a computer-based system having large processor-capacity.

FIGS. 8A-8D illustrate examples of an outer contour 3D-cut of a heart.

Figure 8A:
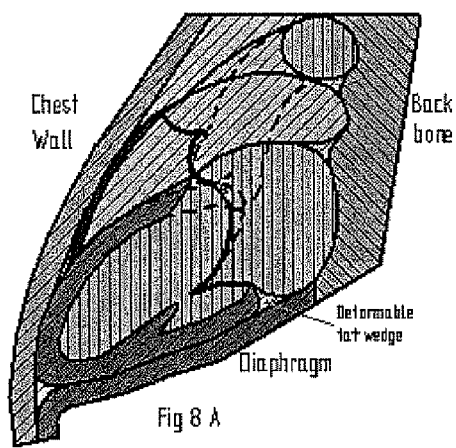

FIG. 8A is a schematic topographic picture of a long axes cut through the heart. Note its location between the thoracic cage and the region of the backbone. The auricles with their appendixes smoothens the edges around Aorta and Pulmonalis at the outflow tract.

Figure 8B:
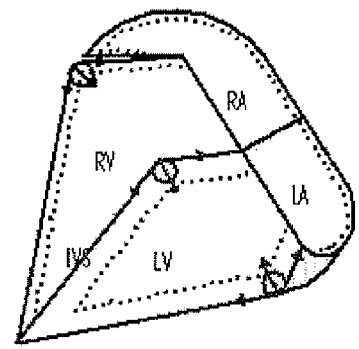

FIG. 8B is a schematic picture of the contours of the surfaces that generates the hearts pumping and regulating functions. The outflow and inflow tracts and valves are not shown. The circles are symbols for the first-class levers functions and the easy sliding that the incompressible blood and the slippery surfaces of the epi- and pericardia create. The arrows indicate the net forces that are needed to balance the hydraulic forces inside the heart. RA and LA stands for Right Atria and Left Atria with the bended parts that corresponds to the auricles and the volume of the deformable fat wedge. RV, LV, and IVS stands for Right Ventricle, Left Ventricle and Inter Ventricular Septum.

Figure 8C:
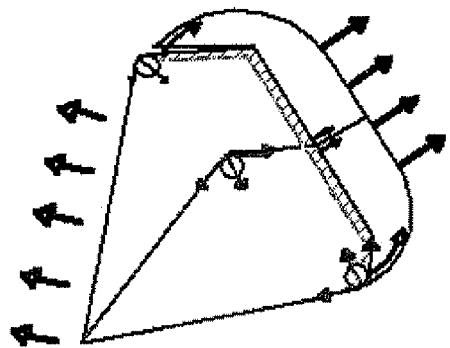

FIG. 8C illustrates the atria contraction that brings the spherical DeltaV-piston to the top of the heart and increases the stroke length of the following ventricular contraction. The large arrows symbolize the strong resistance to motions in these regions.

Figure 8D:
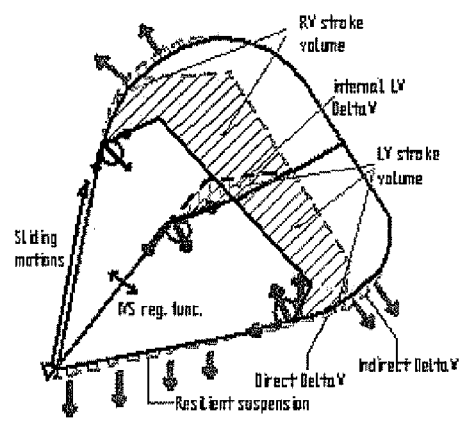

And finally, FIG. 8D demonstrates the piston type pumping function of the DeltaV-piston and demonstrates where to find the volumes that generates the stroke volumes out of the right and left ventricle. Note, that the internal DeltaV-volume "steals" volume from the right ventricle. The areas of the outflow tract are not shown but symbolically included. Note further the sliding motions towards the thoracic cage (chest wall), the resilient suspension and the possible motions of IVS.

FIG. 9 schematically illustrates the graphical user interface according to the present invention, where bar graphs illustrate the temporal duration of different states (upper bar graph) in relation to an ECG signal variation in relation to the different states (lower bar graph).

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A method for graphical representation of time-related heart cycle state diagrams based on measured heart functions and heart pumping models, the method comprising:
    measuring one or more heart functions of a patient, the measuring selected from one or more of ultrasound imaging, electrocardiogram, magnetic resonance imaging, spinning computer aided tomography, strain rate imaging, x-ray imaging, gamma radiation imaging, pulse plethysmography, oximetry, tissue velocity imaging, pulse measuring, flow measuring, pressure measuring, or volume measuring;
    analyzing the measured heart functions using a dynamic displacement pumping model of a heart using one or more processing devices, the pumping model determining heart cycle states by simulating heart pumping, and by identifying durations of heart cycles, from the measured heart functions; and
    displaying a graphical model of the heart cycle states on a graphical user interface such that a temporal relation between different heart cycle states is depicted in a single state diagram.

2. The method for graphical representation of heart cycle state diagrams based on measured heart functions and heart pumping models according to claim 1, further comprising measuring velocity changes of a heart and using the measured velocity changes as triggering points correlating to hydraulic or mechanical heart activity.

3. The method for graphical representation of heart cycle state diagrams based on measured heart functions and heart pumping models according to claim 1, wherein the different heart cycle states are graphically presented as one or several overlapping diagrams presenting different activities of the heart at one or several locations arranged as heart cycle state diagrams in which heart cycle states are represented as segments of a circle having lengths corresponding to a duration of heart cycle state.

4. The method for graphical representation of heart cycle state diagrams based on measured heart functions and heart pumping models according to claim 3, wherein the different activities of the heart are represented by three or more rings in which a first ring represents a state diagram from a left ventricle, a second ring represents a state diagram from a right ventricle and a third ring positioned between the first and second rings represents a state diagram of a ventricular septum.

5. The method for graphical representation of heart cycle state diagrams based on measured heart functions and heart pumping models according to claim 3, wherein the heart cycle states are graphically presented in one or more bar graphs divided into parts, each part representing different states and wherein a size of each part correlates to a duration of a respective heart cycle state.

6. The method for graphical representation of heart cycle state diagrams based on measured heart functions and heart pumping models according to claim 5, wherein a first bar graph represents states of a right heart half and a second bar graph represents states of a left heart half.

7. The method for graphical representation of heart cycle state diagrams based on measured heart functions and heart pumping models according to claim 6, further comprising a third bar graph that represents a state diagram of activities of an interventricular septum.

8. The method for graphical representation of heart cycle state diagrams based on measured heart functions and heart pumping models according to claim 1, wherein each presented heart cycle state is depicted in one or more of a different predetermined color or pattern.

9. The method for graphical representation of heart cycle state diagrams based on measured heart functions and heart pumping models according to claim 8, further comprising coding different heart cycle states.

10. The method for graphical representation of heart cycle state diagrams based on measured heart functions and heart pumping models according to claim 8, further comprising percentage scoring of heart cycle states.

11. The method for graphical representation of heart cycle state diagrams based on measured heart functions and heart pumping models according to claim 1, further comprising auxiliary input signals to relate heart cycle states for display as a user-specific state diagram.

12. The method for graphical representation of heart cycle state diagrams based on measured heart functions and heart pumping models according to claim 1, wherein the displaying a graphical model of heart cycle states is continuously updated in real time.

13. The method for graphical representation of heart cycle state diagrams based on measured heart functions and heart pumping models according to claim 1, further comprising communication with a remotely-located external database.

14. The method for graphical representation of heart cycle state diagrams based on measured heart functions and heart pumping models according to claim 1, further comprising determining a therapeutic treatment based on the displayed graphical model of heart cycle states.

15. The method for graphical representation of heart cycle state diagrams based on measured heart functions and heart pumping models according to claim 1, wherein the measuring the heart functions comprises obtaining triggering points simultaneously from the left side and the right side of the heart, and the method further comprises displaying two interacting time-related state diagrams based on the simultaneously obtained triggering points from the left side and the right side of the heart.

* * * * *

UNITED STATES PATENT AND TRADEMARK OFFICE
CERTIFICATE OF CORRECTION

PATENT NO.        : 8,560,057 B2                                               Page 1 of 1
APPLICATION NO.   : 12/303154
DATED             : October 15, 2013
INVENTOR(S)       : Stig Lundbäck It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1208 days.

Signed and Sealed this
Fifteenth Day of September, 2015

Michelle K. Lee
*Director of the United States Patent and Trademark Office*